(12) United States Patent
Fontius

(10) Patent No.: US 8,159,224 B2
(45) Date of Patent: Apr. 17, 2012

(54) COMBINED MAGNETIC RESONANCE IMAGING AND TARGETING DEVICE FOR MAGNETIC PARTICLES

(75) Inventor: Jörg Ulrich Fontius, Neunkirchen A. Brand (DE)

(73) Assignee: Siemens Aktiengesellschaft, Munich (DE)

( * ) Notice: Subject to any disclaimer, the term of this patent is extended or adjusted under 35 U.S.C. 154(b) by 400 days.

(21) Appl. No.: 12/568,935

(22) Filed: Sep. 29, 2009

(65) Prior Publication Data

US 2010/0079142 A1    Apr. 1, 2010

(30) Foreign Application Priority Data

Sep. 30, 2008  (DE) .................. 10 2008 049 771

(51) Int. Cl.
*G01V 3/00*    (2006.01)
(52) U.S. Cl. ......................... 324/318; 324/309
(58) Field of Classification Search .......... 324/300–322; 600/407–445; 424/9.2, 9.3; 436/173
See application file for complete search history.

(56) References Cited

U.S. PATENT DOCUMENTS

| | | | |
|---|---|---|---|
| 7,560,096 B2* | 7/2009 | Driehuys et al. | 424/9.3 |
| 2005/0148864 A1 | 7/2005 | Slade et al. | |
| 2008/0214926 A1* | 9/2008 | Fukuta | 600/410 |
| 2009/0297453 A1* | 12/2009 | Driehuys | 424/9.2 |

OTHER PUBLICATIONS

Alexiou et al., "Magnetisches Drug-Targeting—ein neuer Ansatz in der lokoregionalen Tumortherapie mit Chemotherapeutika", HNO 7, Jul. 2005, pp. 618-622, vol. 53(7).
Model Gallery "Magnetic Drug Targeting", 1997-2008 COMSOL AB.
Udrea et al., "An in vitro study of magnetic particle targeting in small blood vessels", 2006 Phys. Med. Biol. 51 4869-4881 doi:10.1088/0031-9155/51/19/010.
Schillemans et al., Future Medicine—Nanomedicine, Jun. 2006, pp. 31-37, 1(1):31—Summary, vol. 1, No. 1, Nanomedicine 1:4, 437-447.

* cited by examiner

*Primary Examiner* — Brij Shrivastav

(57) ABSTRACT

The invention relates to a combined magnetic resonance imaging and targeting device for magnetic particles having a magnetic coil array. The magnetic coil array comprises a plurality of coils, each of which is connected to a power supply. The power supplies are connected to a controller which is embodied for two operating modes. In a first operating mode the power supplies are controlled in such a way that a magnetic field extreme value is generated at least one location in a target region. In a second operating mode the power supplies are controlled in such a way that magnetic fields having a strictly monotonously rising or falling magnetic field profile are generated in an imaging region.

8 Claims, 3 Drawing Sheets

COMBINED MAGNETIC RESONANCE IMAGING AND TARGETING DEVICE FOR MAGNETIC PARTICLES

CROSS REFERENCE TO RELATED APPLICATIONS

This application claims priority of German application No. 10 2008 049 771.1 filed Sep. 30, 2008, which is incorporated by reference herein in its entirety.

FIELD OF THE INVENTION

The invention relates to a combined magnetic resonance imaging and targeting device for magnetic particles having a magnetic coil array.

BACKGROUND OF THE INVENTION

Chemotherapy is a form of medical treatment for cancerous diseases (antineoplastic chemotherapy) or infections (anti-infective chemotherapy, also antimicrobial chemotherapy). It uses substances which exert their damaging effect in an optimally targeted manner on specific pathogenic cells or microorganisms and kill off the latter or inhibit them in their growth. With this approach advantage is taken of the different structure of multi-cell (human being) and single-cell organisms (bacteria) in the treatment of bacterial infectious diseases. In the treatment of malignant tumors most of these substances exploit the ability of the tumor cells to divide rapidly, since these cells are more sensitive in their reaction to cell division malfunctions than healthy cells. However, said substances have a similar effect on healthy cells with a similarly efficient ability to divide, as a result of which side-effects such as hair loss or diarrhea can occur.

The desire to treat diseased compartments of the body completely without distributing the chemotherapeutic agent in the remaining healthy organism cannot be adequately realized using the systemic application routes known in the prior art. Different regional and targeted pharmaceutical applications have been developed in the last 20 years in order to protect healthy cells against increased exposure and achieve a higher concentration of the active agent in the area of application, e.g. a tumor.

Magnetic guidance of pharmaceuticals, also known as drug targeting, is one possibility of targeted tumor treatment. With this approach, chemotherapeutic agents, such as e.g. cytostatic drugs, are reversibly bound to ferrofluids, which are colloidal solutions of magnetic nanoparticles, and applied intravascularly. Said ferrofluids are then concentrated in a specific compartment of the body by exposure to an external magnetic field. They serve as transportation vehicles for concentrating the bound chemotherapeutic agents in the desired target region via the bloodstream when a corresponding magnetic field is focused over said region.

With many diseases it is desirable to perform diagnosis and treatment ideally simultaneously in a cohesive process without the need to reposition the patient.

SUMMARY OF THE INVENTION

The object underlying the invention is therefore to disclose a combined treatment and diagnostic device by means of which it is possible to guide magnetic particles to a target while at the same time performing diagnostic monitoring.

The object is achieved according to the invention by the device disclosed in the claims. According thereto, the invention is realized on a combined magnetic resonance imaging and targeting device for magnetic particles having a magnetic coil array.

According to the inventive solution path, the device is characterized in that the magnetic coil array comprises a plurality of coils, each of which is connected to a power supply, that the power supplies are connected to a controller which is embodied for two operating modes, the power supplies being controlled in a first operating mode in such a way that a magnetic field extreme value is generated at at least one location in a target region, and the power supplies being controlled in a second operating mode in such a way that a magnetic field having a magnetic field profile suitable for the imaging is generated in an imaging region.

In this way a diagnostic magnetic resonance device is trained for guiding magnetic particles to a target such that it is made possible to perform a diagnosis and a targeting of magnetic particles to which corresponding medicines are bound in immediate succession without the need to reposition the patient. The magnetic particles represent small magnetic poles on which magnetic fields, in particular inhomogeneous magnetic fields, exert a force. With the aid of the magnetic coil array contained in the magnetic resonance device the magnetic particles are guided to the treatment location in the target region, the targeting being performed by means of special location-dependent magnetic fields. By means of the array structure it is possible to generate strictly monotonously rising or falling field profiles, hereinafter also referred to as gradient fields, in the imaging region and the target region and in addition in the target region also field profiles having a magnetic field extreme value. The field forming is performed in all three spatial axes, with the result that both a position encoding of the image signals and a concentration of the magnetic particles can be achieved at a desired location in the target region. During the targeting it is also possible to exploit the effect that gradient fields tend to possess a translational rather than a focusing effect, as is the case with fields that have a magnetic field extreme value.

Given an appropriate localization geometry of the magnetic particles it is even possible to activate the first and second operating modes simultaneously. For example, a localization geometry that runs in an entire plane, e.g. a transversal plane, would be suitable for the simultaneously activated operating modes.

The geometry and the profile of the target region can be drawn in an overview image, for example graphically by way of an input device, e.g. a computer mouse. The currents to be provided by the power supplies are then calculated on a computer as a function of the profile of the target region.

For the guiding of the magnetic particles to the target it is thus of particular advantage that magnetic resonance imaging and consequently diagnostic monitoring can be performed during the treatment without the need to reposition the patient. The gradient fields necessary for the position encoding during the imaging are generated by switching over the operating mode of the controller. By means of the imaging it can then be checked whether the magnetic particles have also reached the target volume. If this is not yet the case, the magnetic particles can be relocalized or, as the case may be, refocused in the first operating mode of the controller. In this case, however, care should be taken to ensure that the magnetic particles are not delocalized again by the gradient fields during the imaging. This can be achieved for the imaging by means of a short measuring duration and/or small amplitudes for the imaging magnetic field compared to the magnetic field for the localization.

A further application of the combined magnetic resonance imaging and targeting device consists in its use in multicomponent therapy. In this case use is made of two reagents which are chemically inactive when separate from each other. When they come together, however, they react, generating heat in the process for example. With the aid of the magnetic carrier particles the first chemically inactive reagent can then be guided to the location of the tumor by magnetic targeting. Once it is focused there, the patient is injected with the second chemically inactive reagent so that it can disperse in the body. When the second reagent now meets the first reagent, a thermal, e.g. exothermic, reaction takes place, the resulting heat generation of which produces the desired therapeutic effect, e.g. a tumor requiring to be treated is damaged. A number of advantages result from the use of a plurality of components. For example, no time dependence exists in the targeting of the magnetic particles. In the case of a thermal reaction the occurring temperature distribution can also be measured in a spatially resolved manner with the aid of magnetic resonance methods. Similarly, the degree of destruction of a treated tumor can also be determined. In addition it would also be possible to use a further substance which releases the reagent from the carrier magnetic particles again such that although the reagent still remains detectable using magnetic resonance methods (e.g. by means of molecular imaging), a delocalization due to the gradient fields cannot take place during the imaging.

The dependent claims disclose embodiment variants of the invention.

BRIEF DESCRIPTION OF THE DRAWINGS

An exemplary embodiment of the invention is explained below with reference to five figures, in which.

DETAILED DESCRIPTION OF THE INVENTION

Figure 1:
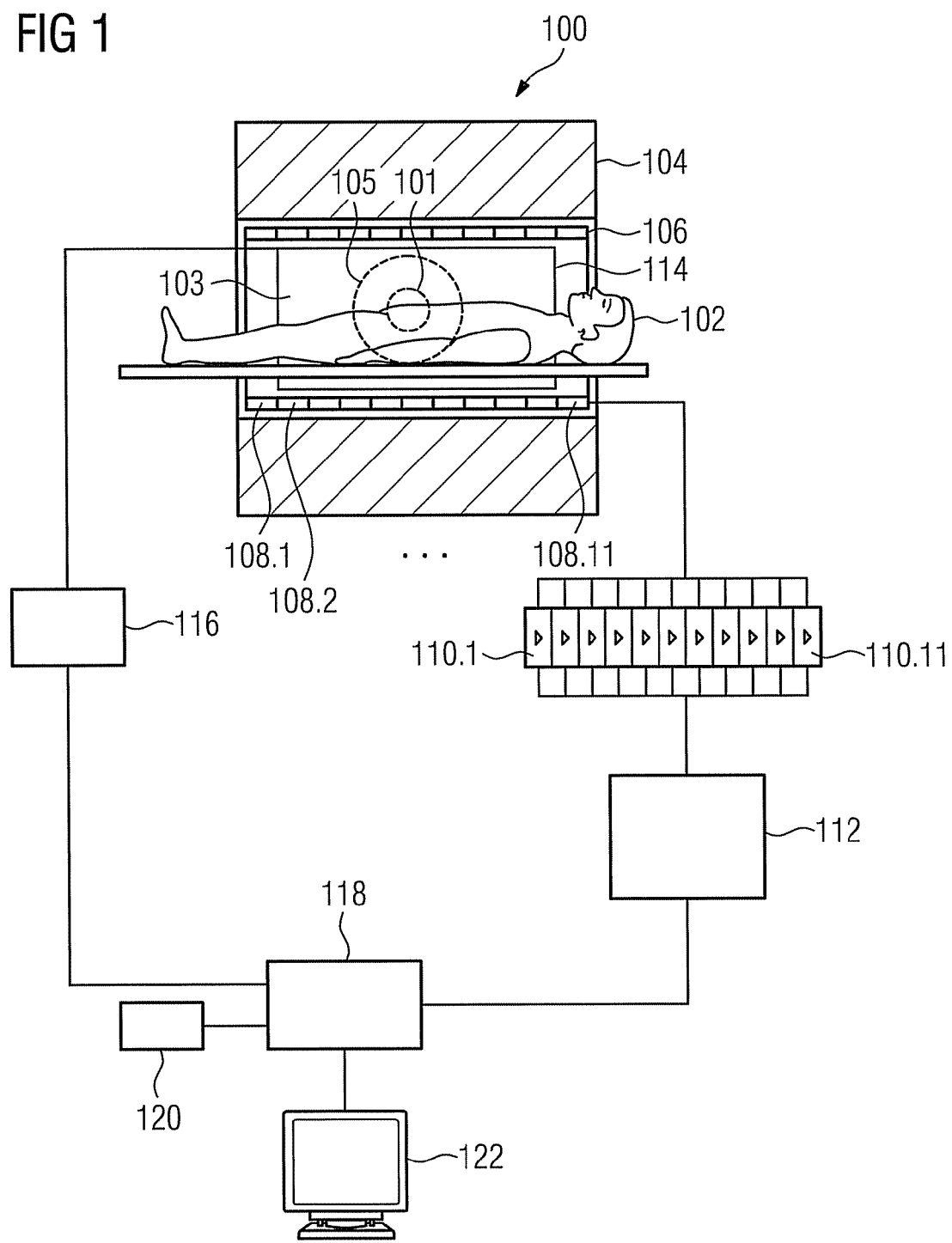
FIG. 1 is an overview representation showing the main components of a combined magnetic resonance imaging and targeting device having a magnetic coil array comprising a plurality of coils.

FIG. 1 shows a combined diagnostic magnetic resonance imaging and targeting device 100 by means of which, in addition to the magnetic resonance imaging, magnetic particles can also be guided into a target region 101 inside a patient 102. Arranged in a tunnel-shaped interior space 103 of a magnet, preferably a superconducting magnet, 104 is a tubular support 106 having in this case, by way of example, 11 coils 108.1 to 108.11. In an imaging region 105 the magnet 104 generates a homogeneous magnetic field in the longitudinal direction of the tubular interior space 103. In a Cartesian coordinate system the z-axis is assigned to this direction. In this case the imaging region 105 is embodied in the shape of a sphere, the target region 101 being located fully within the imaging region 105.

The coils 108.1 to 108.11 comprise both saddle-coil-shaped conductor arrangements for generating location-dependent magnetic fields in the x- and y-direction and annular conductor arrangements for generating location-dependent magnetic fields in the z-direction. The individual coils 108.1 to 108.11 are each connected to a power supply 110.1 to 110.11. The power supplies 110.1 to 110.11 are individually controlled by a controller 112 in multiple operating modes, as described in more detail below.

Arranged within the tubular support 106 for the purpose of exciting and receiving magnetic resonance signals is a high-frequency antenna 114 that is connected to a high-frequency system 116. A central controller 118 controls the entire operation of the combined magnetic resonance imaging and targeting device 100. An input unit 120 permits a user to input corresponding control commands, such as e.g. for controlling the operating modes, the position of the target region 105, the pulse sequence to be activated for recording the image, the image recording parameters, etc. Also present, finally, is a display unit 122 by means of which the user inputs, the position of the target region and the generated magnetic resonance images can be presented to the user for therapy monitoring purposes.

The geometry and the profile of the target region can be drawn e.g. graphically by way of the input unit 120, which includes a computer mouse, for example, into an overview image presented on the display unit 122. The current distribution for the coils 108.1 to 108.11 in the magnetic coil array is calculated as a function of the profile of the target region 101 on a host computer which is implemented e.g. in the central controller 118.

Except for the modified magnetic coil array having the coils 108.1 to 108.11 and the power supplies 110.1 to 110.11 as well as the correspondingly modified controller 112 and central controller 118, the combined magnetic resonance imaging and targeting device corresponds to a conventional diagnostic magnetic resonance device.

The coils 108.1 to 108.11 can be individually controlled in the manner of an array by way of the power supplies 110.1 to 110.11 by means of predefined currents for generating the desired location-dependent and time-variable magnetic field.

Figure 2:
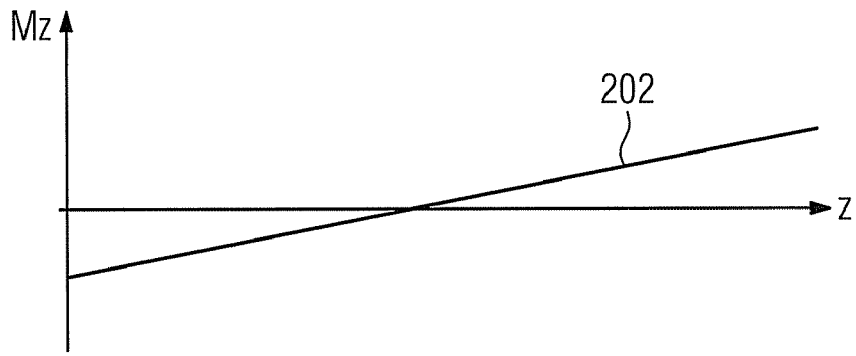
FIG. 2 is a schematic representation showing a first location-dependent profile of the magnetic field in the z-direction.

FIG. 2 shows by way of example the profile 202 of a linearly location-dependent magnetic field Mz in the longitudinal direction of the tunnel-shaped interior space 103, that is to say in the z-direction, in a first or second operating mode. In the first operating mode of the magnetic coil array, magnetic particles are guided to a target, and in the second operating mode imaging is carried out for the purpose of diagnostic monitoring of the progress of the targeting. The gradient field is used during the imaging for the position encoding of the magnetic resonance signals and during the targeting for generating a translational movement of the magnetic particles. Gradient fields are also used in the two other spatial directions (x- and y-axis of the Cartesian coordinate system) for imaging as well as for the corresponding generation of translational movements. The coils 108.1 to 108.11 possess an appropriate design so that by means of a predefined current distribution of the currents from the power supplies 110.1 to 110.11 for the individual coils 108.1 to 108.11 the desired profile of the magnetic fields can be generated not only in the z-direction but also in the other two spatial directions x and y.

Figure 3:
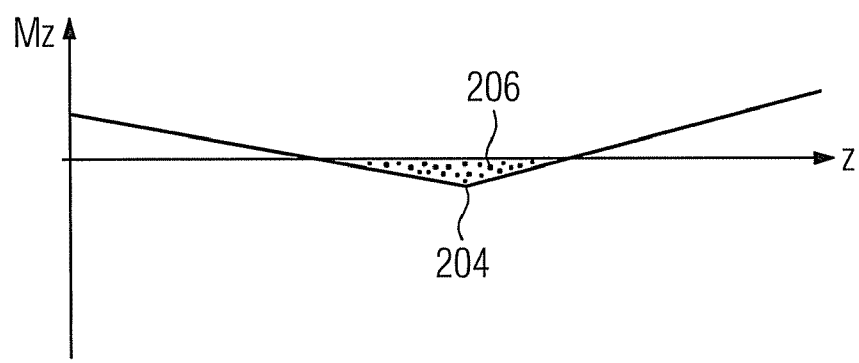
FIG. 3 is a schematic representation showing a second location-dependent profile of the magnetic field in the z-direction.

Essentially, a local extreme value, preferably a minimum, of the magnetic field is used for focusing the magnetic particles in the target region 101. In the first operating mode an inhomogeneous magnetic field is therefore generated having a local minimum 204 in the z-direction with a section-wise linear profile, as shown in FIG. 3. The local minimum 204 is generated with the shown exemplary magnetic field profile in the z-direction at a specific location in the target region such that the magnetic particles 206 are concentrated there. The minima of the magnetic fields in the x- and y-direction are also generated analogously in the target region 101 (not shown here). The magnetic field profile shown in FIG. 3 possesses only one minimum. A plurality of extreme values can also occur in order to allow more degrees of freedom in the calculation of an optimal current distribution. For that purpose a pre-focusing on a minimum is necessary. Here too, corresponding magnetic fields are generated in the two other spatial directions x and y, such that a local minimum results in the target region 101.

For imaging purposes the zero magnetic field value of the gradient field is generally located in the point of origin of the Cartesian coordinate system, which in turn is located in the center of the imaging region 105. For guiding the magnetic particles to the target region 101, the magnetic field, in particular the position of the magnetic field minimum 204, can on the one hand be modified via a corresponding feeding of current to the coils 108.1 to 108.11. On the other hand the position of the patient 102 can also be changed by means of the patient examination couch in order to enable the particles introduced into the body to be concentrated as rapidly as possible in the target region 101.

Figure 4:
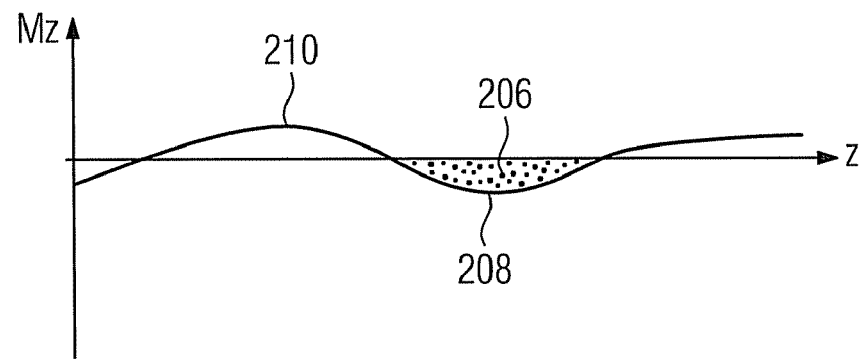
FIG. 4 is a schematic representation showing a third location-dependent profile of the magnetic field in the z-direction.

For targeting purposes FIG. 4 shows a section-wise parabolic profile 210 of the magnetic field Mz in the z-direction in the first operating mode. The figure shows a parabolic local minimum 208 which comprises a relatively large target region 101. In addition there is also a magnetic field maximum 210, though this is located outside of the actual target region 101. Here too, location-dependent magnetic fields are additionally generated in the other spatial directions. As FIG. 4 is intended to illustrate, the steepness of the gradient determines the extension of the target region 101 or, as the case may be, the focusing of the magnetic particles in the target region 101. In order to increase the effectiveness of the targeting in the x- and y-direction, the base magnetic field $B_0$ in the localization volume can be compensated by the z array coils, while localization is performed in the x- and y-direction.

Figure 5:
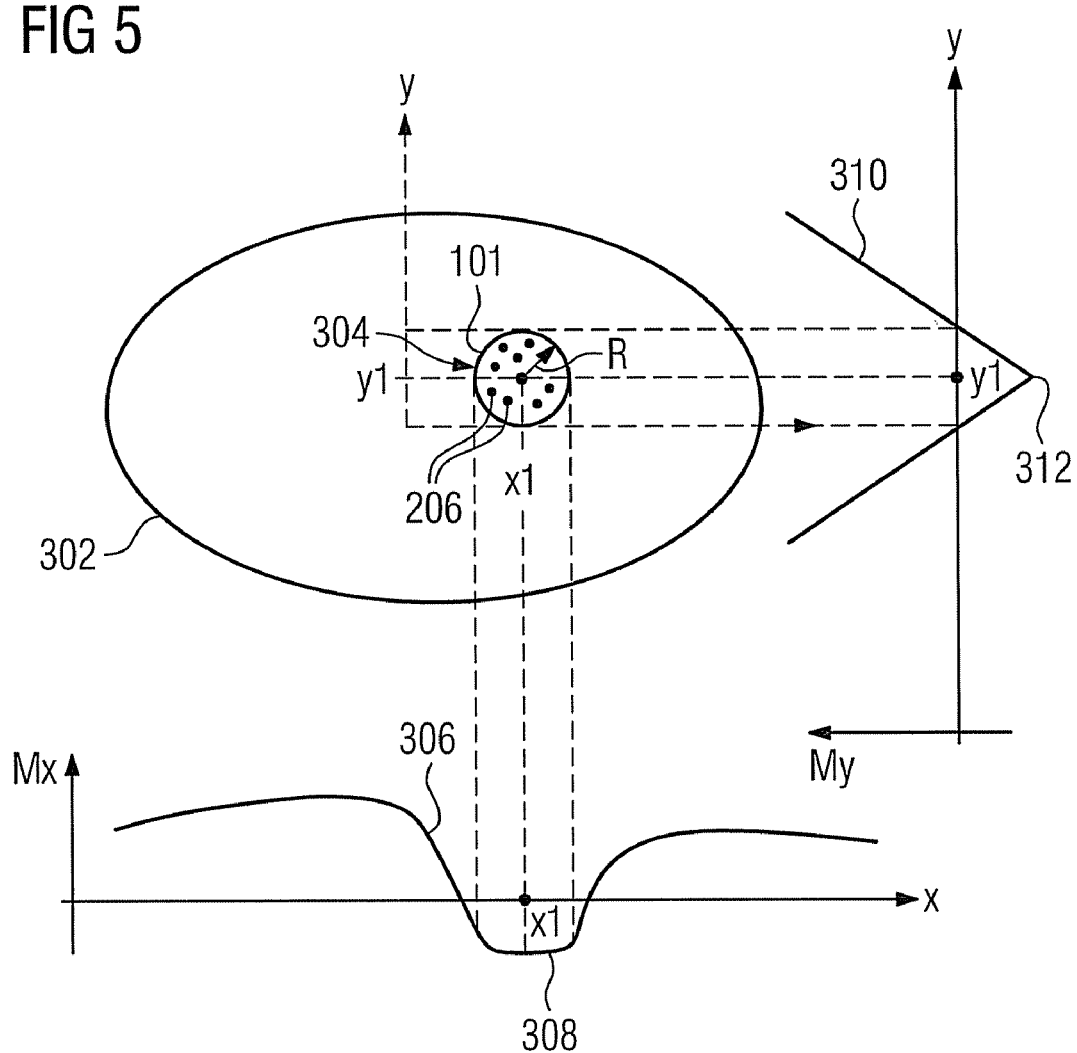
FIG. 5 is a schematic representation showing the position of a magnetic field extreme value in the patient.

FIG. 5 illustrates the position of the target region 101 with the location-dependent magnetic fields used with the aid of a cross-section 302 arranged at the location z1 in the z-direction inside the patient 102. A tumor 304 is located in the cross-section 302 with its center at the point x1, y1 and at the location z1 of the cross-section. The dimensions of the tumor 304 are registered approximately by means of a circle with the radius R. The tumor 304 represents the target region 101 for focusing magnetic particles 206, to which a drug that is to be applied is bound. The magnetic field by means of which the magnetic particles 206 are to be focused in the tumor 304 has its minimum at the point x1, y1 in the cross-section 302. A magnetic field profile 306 is generated by means of the coils for generating a magnetic field Mx varying in the x-direction, said magnetic field profile 306 being embodied in a parabolic shape in its minimum 308. By means of the coils for generating a magnetic field Mx varying in the y-direction, a magnetic field profile 310 is generated with a minimum 312. The magnetic field profile 310 essentially has two linear sections. The magnetic field in the z-direction is embodied with a minimum at the location of the cross-section 302, such that the magnetic particles 206 are focused at the location x1, y1, z1. The location-dependent magnetic fields used are generated by means of a corresponding setting of the currents for the individual coils 108.1 to 108.11.

The invention claimed is:

1. A combined magnetic resonance imaging and targeting device having a magnetic coil array for generating a non-stationary and time-dependent magnetic field, comprising:
   a plurality of coils;
   a plurality of power supplies, each of the power supplies being connected to one of the coils respectively; and
   a controller that controls the power supplies in a first operating mode for generating a magnetic field extreme value at a location in a target region of a patient and controls the power supplies in a second operating mode for generating the magnetic field having a strictly monotonously rising or falling magnetic field profile in an imaging region of the patient.

2. The combined magnetic resonance imaging and targeting device as claimed in claim 1, wherein the target region is overlapped with the imaging region.

3. The combined magnetic resonance imaging and targeting device as claimed in claim 1, wherein the target region is coincide with the imaging region.

4. The combined magnetic resonance imaging and targeting device as claimed in claim 1, wherein the magnetic field extreme value is a local minimum value.

5. The combined magnetic resonance imaging and targeting device as claimed in claim 1, wherein the magnetic field profile is linear.

6. The combined magnetic resonance imaging and targeting device as claimed in claim 1, wherein the magnetic field profile is parabolic.

7. The combined magnetic resonance imaging and targeting device as claimed in claim 1, wherein a plurality of field extreme values are generated in a plurality of locations in the target region and the magnetic field profile is a higher-order magnetic field profile between the field extreme values.

8. A method for generating a non-stationary and time-dependent magnetic field by a combined magnetic resonance imaging and targeting device having a magnetic coil array, comprising:
   arranging a plurality of coils in the magnetic coil array;
   connecting each of the coils with one of a plurality of power supplies;
   controlling the power supplies by a controller in a first operating mode for generating a magnetic field extreme value at a location in a target region of a patient; and
   controlling the power supplies in a second operating mode for generating the magnetic field having a strictly monotonously rising or falling magnetic field profile in an imaging region of the patient.

* * * * *